(12) United States Patent
Bloch et al.

(10) Patent No.: US 8,017,318 B1
(45) Date of Patent: Sep. 13, 2011

(54) METHOD FOR DETECTING AND/OR QUANTIFYING A KNOWN FUNCTION FROM A NUCLEIC ACID SAMPLE

(75) Inventors: Jean François Bloch, Nîmes (FR); Sandrine Dautel, Nîmes (FR); Daniel Dupret, Calvisson (FR); Jean-Michel Masson, Toulouse (FR); Fabrice Lefevre, Nîmes (FR)

(73) Assignee: Proteus S.A., Nimes (FR)

( * ) Notice: Subject to any disclaimer, the term of this patent is extended or adjusted under 35 U.S.C. 154(b) by 1556 days.

(21) Appl. No.: 09/722,406

(22) Filed: Nov. 28, 2000

Related U.S. Application Data

(63) Continuation of application No. PCT/FR99/03059, filed on Dec. 8, 1999.

(30) Foreign Application Priority Data

Dec. 8, 1998 (FR) .................................... 98 15487

(51) Int. Cl.
  C12Q 1/68 (2006.01)
  C12P 19/34 (2006.01)
  C07H 21/02 (2006.01)
  C07H 21/04 (2006.01)
(52) U.S. Cl. .......... 435/6; 435/91.2; 536/23.1; 536/24.3
(58) Field of Classification Search ........................ None
  See application file for complete search history.

(56) References Cited

U.S. PATENT DOCUMENTS

| 4,557,862 | A | 12/1985 | Mangel et al. |
| 5,760,207 | A | 6/1998 | Kinzler et al. |
| 2003/0134779 | A1* | 7/2003 | Diarra et al. ...................... 514/6 |

FOREIGN PATENT DOCUMENTS

| EP | 0518557 | | 12/1992 |
| GB | 2276621 | | 10/1994 |
| JP | 07184648 | * | 7/1995 |
| WO | WO92/07949 | | 5/1992 |
| WO | WO94/05812 | | 3/1994 |
| WO | WO94/24303 | | 10/1994 |
| WO | WO95/09925 | | 4/1995 |
| WO | WO96/08580 | | 3/1996 |
| WO | WO 99/11777 | * | 3/1999 |

OTHER PUBLICATIONS

Dunbar et al (J. lmmunol. (1997) 158:4252-4259).*
Gordon et al (EMBO J. (1988) 7(2): 309-317).*
Beaufrere et al (Exp. Eye Res. (1997) 65: 849-854).*
Guatelli et al (Proc. Natl. Acad. Sci. (1990) 87:1874-1878).*
Roest et al (Human Molecular Genetics (1993) 2(1):1719-1721).*
World Health Organization Fact sheet No. 164 (revised Oct. 2000).*
Allen and Miller (1999) Analytical Biochemistry vol. 269: 32-37.*
Damen et al. (1996) Journal of Virological Methods 58: pp. 175-185.*
Jacobs (1996) Seminars in Pediatric Infectious Diseases vol. 7, No. 3: pp. 170-181.*
Chang, C-A. et al., J. Gen. Virol., vol. 69, pp. 1117-1122 (1988).*
Miller, S.A. et al., Ann. Rev. Phytopathol., vol. 26, pp. 409-432 (1988).*
Jensen, S.G. et al., Phytopatology, vol. 76, pp. 528-532 (1986).*
Nuss, D.L. et al., J. Virol., vol. 34, pp. 532-541 (1980).*
Dorsky, D. I. et al., J. virology, vol. 62, pp. 3224-3232 (1988).*
Somogyi, P.A. et al., J. Virol. Meth., vol. 27, pp. 269-276 (1990).*
Suzuki, K. et al., Biotechnol. Appl. Biochem., vol. 18, pp. 37-44 (1993).*
Yu, S-L. et al., J. Virol. Meth., vol. 53, pp. 63-73 (1995).*
Koch, N. et al., J. Clin. Microbiol., vol. 37, pp. 1595-1597 (May 1999).*
Tang, J.R. et al., J. Gen. Virol., vol. 74, pp. 1827-1835 (1993).*
Martemyanov, K.A. et al., FEBS Letters, vol. 414, pp. 268-270 (1997).*
Nam, S. H. et al., J. Virol., vol. 67, pp. 196-203 (1993).*
Song, M-D., Korean Biochem. J., vol. 25, pp. 342-346 (1992).*
Song, M-D., Korean Biochem. J., vol. 25, pp. 342-346 (1992), translation, pp. 1-11.*
Henkel, R. P. et al., "Functional Analysis of Mutated cDNA Clones by Direct Use of PCR Products in In Vitro Transcription/Translation Reactions", *Analytical Biochemistry*, vol. 214, No. 1, pp. 351-352, (1993).
Hoeltke, H. et al., "Biotin In Vitro Translation, Nonradioactive Detection of Cell-Free Synthesized Proteins", *Biotechniques*, vol. 18, No. 5, pp. 900-907, (1995).
Ohuchi et al., "In Vitro Method for the Generation of Protein Libraries Using PCR Amplification of a Single DNA Molecule and Coupled Transcription/Translation", *Nucleic Acids Research*, vol. 26, No. 19, pp. 4339-4346, (1998).
Promega Corp.: "Promega 1997 Catalog", Promega Corp., NSDOCID XP002102864, pp. 2, 117-136 (1997).
Resto et al., "Amplification of Protein Expression in a Cell Free System", *Nucleic Acids Research*, vol. 20, No. 22, pp. 5979-5983; (1992).

* cited by examiner

*Primary Examiner* — Teresa Strzelecka
(74) *Attorney, Agent, or Firm* — Hunton & Williams LLP

(57) ABSTRACT

The invention concerns a method for detecting a known function, from nucleic acids present in a sample, characterized in that it comprises the following steps: (a) preparing, from the nucleic acids of the sample, nucleic acid molecules comprising the gene(s) coding for the protein(s) corresponding to said function, and the control elements required for the transcription and the translation of said gene(s); (b) in vitro transcription and translation of the nucleic acid molecule prepared in step (a); (c) detecting and/or measuring the function corresponding to the protein(s) produced in step (b).

19 Claims, 6 Drawing Sheets

Figure 1:
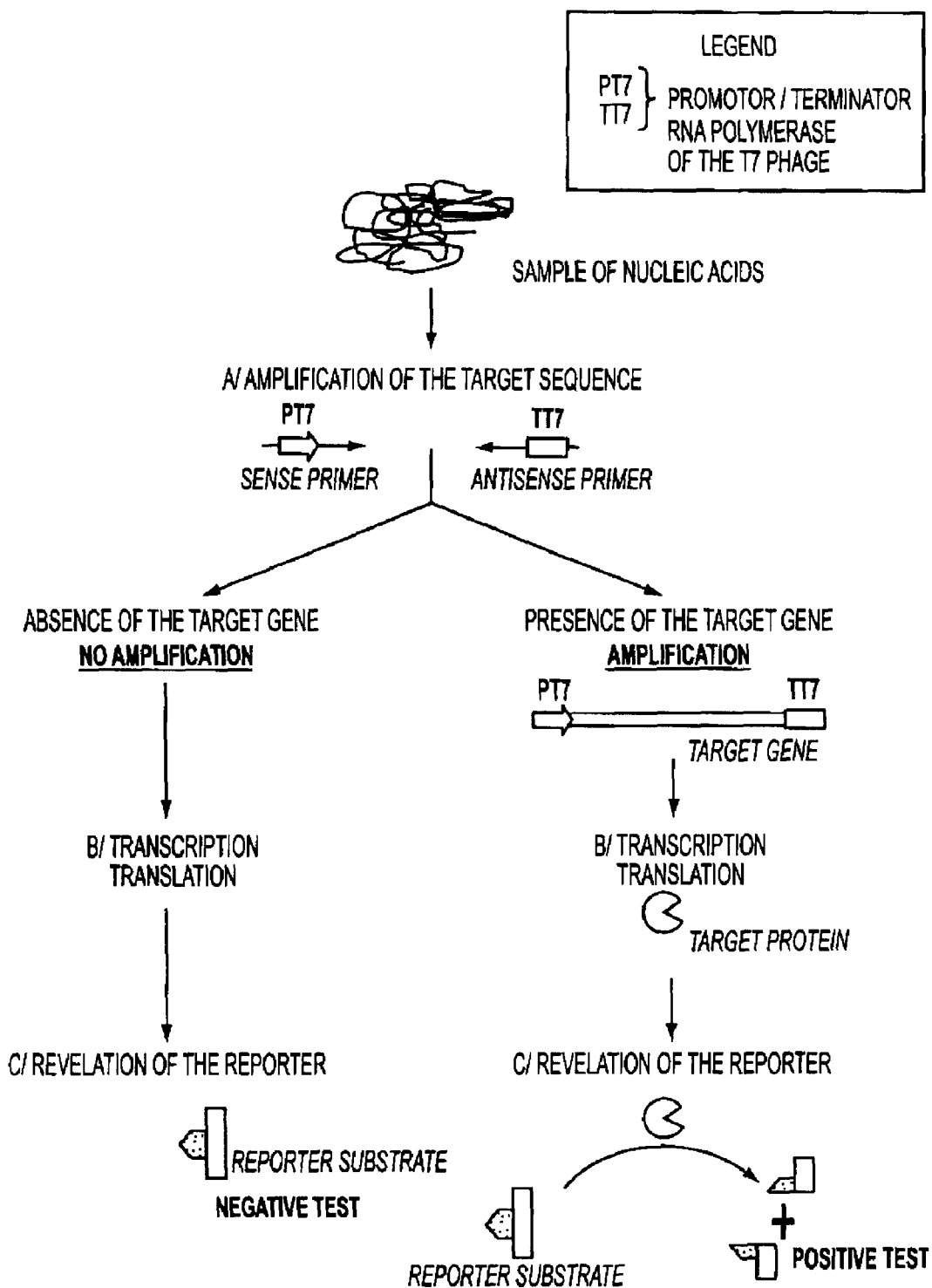

SEQUENCE LISTING

```
<160> NUMBER OF SEQ ID NOS: 1

<210> SEQ ID NO 1
<211> LENGTH: 9
<212> TYPE: PRT
<213> ORGANISM: artificial sequence
<220> FEATURE:
<223> OTHER INFORMATION: protease substrate
<220> FEATURE:
<221> NAME/KEY: MISC_FEATURE
<222> LOCATION: (1)..(1)
<223> OTHER INFORMATION: Xaa = gamma-2-Aminobutyric Acid modified with
      amino-terminal DABCYL Acceptor moiety
<220> FEATURE:
```

-continued

```
<221> NAME/KEY: MISC_FEATURE
<222> LOCATION: (9)..(9)
<223> OTHER INFORMATION: Glutamine modified with carboxy-terminal EDANS
      Donor moiety

<400> SEQUENCE: 1

Xaa Ser Gln Asn Tyr Pro Ile Val Gln
1               5
```

METHOD FOR DETECTING AND/OR QUANTIFYING A KNOWN FUNCTION FROM A NUCLEIC ACID SAMPLE

CROSS-REFERENCE TO RELATED APPLICATIONS

This application is a continuation of International Application No. PCT/FR99/03059, filed Dec. 8, 1999, which claims priority to French Patent Application No. FR98/15487, filed Dec. 8, 1998.

The present invention has for its object a method of detectiing and/or of quantifying a known function starting from a sample of nucleic acids. The method of the invention notably finds application in the in vitro analysis of a known function starting from a sample of nucleic acids. This method also finds application in the diagnostic area, where the sought-after function is characterized for example by the presence of enzymatic activity, of cancer cells, of pathogenic organisms (bacteria or viruses), of a specific mutation, of a foreign gene.

Today, the search for target polynucleotide sequences represents a major objective in a number of research laboratories involved in numerous areas of activity and principally in the medical, agribusiness or chemical industry fields. In these fields, the search for target sequences has as its aim for example:

The diagnosis of viruses at the origin of diseases such as AIDS (HIV) or hepatitis B (HBV).

The specific diagnosis of diseases of bacterial origin, such as tuberculosis or leprosy.

The diagnosis of mutations at the origin of genetic diseases or cellular cancers.

The diagnosis of bacterial contamination in an agribusiness food chain.

The search for microorganisms involved in the biological corrosion of pipes or of containers used in industrial processes.

The major difficulty of the methods of diagnosis used in the prior art resides in the specificity, the sensitivity, the rapidity and the reproducibility of the diagnostic test used. It is essential to be able to provide a clear result. It is therefore advisable to have at one's disposal a method that can be carried out starting from an initial sample of whatever nature or origin. It is also necessary that the method permit a reduction in false positives due to the composition of the sample or generated by the method reduced to practice.

Now, as previously indicated, the methods of the prior art are essentially based on the detection of nucleic acid fragments that permit possible quantification of a gene. Among these, there can be cited:

Tests using genetic probes, where the quantity of target sequence detected depends on the size and on the homology of the probe. These tests are applied to the detection of different organisms, such as bacteria, viruses, mycobacteria, fungi or other parasites. The problem with these tests resides in their low sensitivity.

PCR type amplification tests or others that permit specific detection of genetic information with a real sensitivity, but which all the same must be verified due to technical problems leading to false positives.

During a diagnosis of sequences by PCR amplification, there is not certainty about the nature of the amplicon, and in the case where the analyzed protein is sought-after by immunodetection, the results can correspond to a non-specific cross-reaction. In addition, in both cases, the activity of the sought-after protein is not known.

In addition, these detection tests do not permit obtaining information on the functional activity of the product of the gene, which can:

Create false positives during the detection of homologous sequences instead of the target sequence, Create diagnostic errors, as in the case of the detection of a mutated gene which codes for a non-functional protein, End up with an insufficient level of information, as for example the detection of a pathogen without giving so much as an indication of its virulence or its sensitivity to a treatment, which leads to a characterization defect, End up (with) too low a sensitivity threshold.

There can also be cited immunological or radioactive incorporation tests during synthesis of proteins, which permits detection and possibly direct quantification of a protein. Antibodies are in effect routinely used to specifically identify an antigen in a sample. However, these tests generally do not provide information on the functional activity of the protein.

There equally exists in the prior art tests permitting the direct carrying out of the detection of a function starting from a sample without going through the nucleic acids present in said sample. It thus relates to working directly on a collection of factors present in the sample and susceptible to modify a functional test. However, it will not be possible to distinguish a single function coming from two different factors. It can for example relate to a function associated with two different viruses, which it will not be possible to distinguish with the same functional test. There can be cited for example the detection of the reverse transcriptase functional activity proposed in the PCT patent application published under the number WO96/23076, wherein it was not possible to determine if the reverse transcriptase activity came from HIV or from another virus.

There can finally be cited the tests for detecting the function and the functional variants based on the steps carried out in vivo such as antibiograms or techniques of phenotype tests for example on the HIV virus. If the manipulated strains are dangerous, they require specific safety conditions and therefore special laying out of laboratories. In addition to their implementation complexity that makes them difficult to automate, these tests are costly and are long and tedious to implement. Thus, in the case of viruses, the isolation of the viruses lasts from 4 to 10 weeks. More recent tests based on methods of cloning of enzymatic activity still take from 3 to 4 weeks. In addition, these tests do not always permit detection of minor variants.

The object of the present invention is precisely to offer a method of detection and advantageously of quantification of a known function possibly present in a sample, which does not give rise to the disadvantages set forth above. The method of the invention is applicable, as is understood, to the detection and/or the simultaneous or non-simultaneous quantification of one or several known functions present in the same sample or in different samples that have been grouped together. Thus, the use of the term "function" hereinafter in the singular will equally cover the term "functions" in the plural and vice versa, except when it is explicitly indicated that it relates to the implementation of the method of the invention to several functions. The method of the invention therefore permits not only the detection and advantageously the quantification of one or several functions, but also their characterization from a biochemical perspective starting from a single sample.

It is understood that function is the activity of one or several specific proteins of at least an organism or at least of a process, and that it is detected and/or quantified according to the present invention by the expedient of a test of the function of one of said proteins. In the scope of this invention, the phenotype is considered as a function. The method of the invention therefore more particularly finds its application in the field of in vitro diagnosis and notably in the matter of analysis of a function. In effect, it is also understood that by function, in the sense of the present invention, is meant the demonstration of an observable property corresponding to the expression of one or several genes. This demonstration can be translated into the expression of a morphologic trait, of a clinical syndrome, of a resistance to a toxic compound, of the activity of a protein or also to the production of a substance such as a metabolite, antibiotic, etc. In the scope of this definition of the function, the invention also permits the in vitro analysis of a function corresponding to the result of the expression of several genes, the corresponding proteins all being necessary to the expression of said function. In this form of carrying out the invention, the genes coding for this or these functions can be located:

On the same DNA fragment, in the case of a phenotype expressed by an operon,

At different places of the DNA genome, in the case of certain metabolic pathways.

The analyzed phenotype according to the process of the invention can therefore not be only that associated with a protein, but that associated with a collection of proteins. It relates for example, as indicated previously, to a phenotype corresponding to the synthesis of a metabolite (energetic metabolite, antibiotic, etc.), to the degradation of a compound (of the nutriment or xenobiotic type) or to the collection of a complex protein comprised of several identical or different sub-units.

The function can correspond for example to an enzymatic activity or an affinity. In the scope of the identified enzymatic activity, a person skilled in the art, to demonstrate the presence of the sought-after function, can contemplate any type of specific substrate. The person skilled in the art can for example refer to the works such as Methods In Enzymology or Annual Review of Biochemistry, in which a large number of methods of enzyme analysis and of preparation of substrates are described. In the case of the highlighting of an affinity, for example of an antigen for an antibody, of a protein for DNA, of a receptor for a ligand etc., the highlighting of a function can be carried out for example by tests such as the binding of labeled ligands by an isotope or by an enzyme or by a fluorophore, by an immunological detection using antibodies labeled with a metal or by an enzyme or by a fluorophore.

Organism is understood as any type of organism or microorganism, such as viruses, bacteria, algae, fungi, or any product containing synthetic or natural nucleic acids permitting the expression of sought-after functions by the process of the invention.

Process is understood as the development of a disease, of an infection or of for example cancerous cells or of contaminants. These processes can take place on a host or in an industrial process.

Translation extract is understood as an extract containing any of the factors necessary to the translation step starting from neosynthetic messengers such as for example ribosomes, tRNA, elongation factors, initiation factors, etc.

Known function is understood as the function which is analyzed according to the process of the invention and which can be detected and/or measured by a functional test.

The biological material from which one obtains the sample on which the method of the present invention is carried out can be any sample liable to contain human, animal, vegetable, microbial, viral type nucleic acids or samples coming from the ground, the water, from a biopsy, diverse cells, a process or an organism. These samples can also correspond to products of any method of amplification of genomic DNA, of synthetic DNA, of RNA, or any nucleic acid product resulting from treatments currently used by a person skilled in the art. It is also well understood that it relates to a crude biological sample such as blood, tissues, urine or any other body fluid such as cerebrospinal, synovial, pleural, pericardial, or previously treated for preparation of the nucleic acids that it contains.

The present invention therefore has as its object a method for detection and/or quantifying a known function, starting from nucleic acids present in said sample, characterized in that it includes the following steps:

a) The preparation, starting from nucleic acids of the sample, of nucleic acid molecules comprising the gene or genes coding for the protein or proteins corresponding to said function, and the control elements necessary for the transcription and for the translation of said gene or genes.

b) The transcription and the translation in vitro of the nucleic acid molecule or molecules prepared at step (a);

c) The detection and/or the measure of the function corresponding to the protein or proteins produced at step (b).

When the process of the invention is a detection method, at least one nucleic acid molecule comprising the gene or genes coding for the protein or proteins corresponding to said function is/are prepared at step (a). More preferably, when the method of the invention is a quantifying method, a quantity of nucleic acid molecules proportional to the quantity of said gene or genes possibly present in the nucleic acids of the sample are prepared. Consequently, the processes implemented at step (a) as described hereinafter are implemented in such a manner as to assure this proportionality.

In order to facilitate the explanation of the invention, any nucleic acid is sequence permitting the expression of the protein or proteins corresponding to the function detected are designated under the term gene at step (a) of the method of the invention. It therefore relates to a DNA or to an RNA sequence.

The detection and/or the measure of the function corresponding to the protein or proteins produced at step (b) is carried out by any functional test of said protein or proteins selected by a person skilled in the art. If the nucleic acids are present in the sample, the function is detected or measured directly or indirectly by one or several functional tests of the protein or proteins produced at step (b). The detection and/or the measure of the function corresponding to the protein or proteins produced at step (b) can make use of, at one of the steps (a) and/or (b) and/or (c), one or several reporter molecules permitting the revealing of the presence of the analyzed function or functions characteristic of the process or of an organism.

The reporter molecule, if it is present, can be any substance capable of directly or indirectly revealing the known sought-after function coded by the protein or proteins expressed at step (b), such as a nucleic acid molecule, a protein, a peptide, such as an antibody or a mixture of antibodies specific to a protein and capable of revealing its activity, or a substrate or a cascade of substrates, wherein one is the enzyme corresponding to the sought-after function, or any chemical or organic or synthetic molecule.

In this way, at step (c), the contacting of the reporter molecule with the proteins possibly expressed at step (b) can be carried out by addition of the reporter molecule in the reaction mixture resulting from step (b). But the reporter molecule can also be present in the reaction mixture from one of the steps (a) or (b), either under its final form as a reporter molecule or, according to a particular form of carrying out the invention, under the form of a nucleic acid molecule (DNA, or RNA) corresponding to the gene coding for said reporter molecule, and then designated hereinafter as a reporter gene. In this particular embodiment, the reporter molecule will be produced during step (b) jointly with the protein or proteins corresponding to the sought-after function.

In this particular form of implementing the method of the invention, the reporter gene is placed under the same control regulatory sequences of transcription and translation as the gene or genes coding for the protein or proteins corresponding to the function analyzed, in such a way to be co-expressed with the latter thus permitting the reporter molecule to be present during step (c). The reporter gene with its regulatory transcription and translation sequences is present under any nucleic acid form as an in vitro expression vector.

By way of example, the reporter gene can be the gene of the protein GFP (Green Fluorescent Protein) or that of the beta-lactamase (TEM-1).

In the case of the GFP, step (c) includes the detection and the quantifying of the fluorescent emission. In this way, the method of the invention permits for example the carrying out of a test such that the GFP is fluorescent only if the target sequence is absent from the nucleic acid sequence studied. It is useful to note that the reporter gene of the GFP presents the advantage of producing a protein having an instantly measurable activity, which permits a supplemental saving in time.

In the case of the beta-lactamase, step (c) includes the measure of the activity of this enzyme, by incubating a fraction of the translation reaction in a buffer containing some nitrocephine. Nitrocephine is a chromogenic beta-lactamine that has the property of changing color from yellow to red when it is hydrolyzed by an active beta-lactamase. A red test indicates for example that the target sequence is present in the nucleic acid sample analyzed.

Any other reporter can be contemplated in the scope of the method of the invention, such as for example genes coding for the beta-galactosidase, luciferase, peroxidase or microperoxidase etc. It should be noted that a reporter gene corresponding to a protein having an enzymatic activity gives rise to a large sensitivity due to the enzymatic multiplier coefficient.

The method of the invention therefore offers a large choice in implementation starting with genes and reporter molecules chosen according to the nature and the activity of the protein or proteins corresponding to the sought-after function.

The measure of the activity of one or several proteins at step (c) can be directly read in a fluorimeter if the measurement of the function makes use of a fluorophore such as for example GFP or of colorimeter if the measure of the function makes use of a chromophore such as for example nitrocephine. But one can equally contemplate measuring by absorbance, by viscometer, by mass spectrophotometer or any other method tied to the measure of the function at step (c). It is quite possible to contemplate continuously carrying out a reading of the function, if the functional test lends itself to it.

As indicated previously the function analyzed can correspond to a single protein or to several proteins, such as for example in the case of a phenotype expressed by an operon. Consequently, the method of the invention can be carried out in several ways.

When the detected and/or quantified function corresponds to a single protein, the method of the invention includes the following steps (a) to (c):
a) The preparation, starting from the nucleic acid sample, of nucleic acid molecules comprising the gene coding for the protein corresponding to said function, 5' of said gene an RNA polymerase promoter and a ribosome binding site, and possibly a RNA polymerase terminator 3' of said gene.
b) The transcription and translation in vitro of the nucleic acid molecule prepared at step (a), possibly in the presence of one or several reporter molecules permitting the revealing and/or the measuring of the activity, the presence or absence of the protein corresponding to said function;
c) The putting into contact of the proteins possibly produced at step (b) with one or several reporter molecules, if the latter were not present at step (b), permitting the revealing and/or the measuring of the activity, the presence of the protein corresponding to said function.

But the method of the invention can also be applied to the detection and/or the quantification of a function corresponding to a collection of proteins. The genes coding for these proteins can be located on the same DNA fragment as in the case of an operon, or at different places of the genomic DNA as in the case of certain metabolic pathways.

When the known analyzed function corresponds to several proteins, step (a) of the method of the invention admits of the following two forms of implementation:
i) Either, said genes are collected under the form of an operon, and then step (a) consists of preparing, starting from a sample of nucleic acids, a nucleic acid molecule comprising genes (the operon) coding for proteins corresponding to said function, if they are present in the nucleic acids of the sample, 5' of the collection of said genes of an RNA polymerase promoter, possibly 3' of the collection of said genes of an RNA polymerase terminator, and for each of said genes its natural ribosome binding site.
ii) Or, said genes are separated and then step (a) consists of preparing, starting from the sample of nucleic acid, one or several nucleic acid molecules comprising the genes coding for the proteins corresponding to said function, if they are present in the nucleic acids of the sample, 5' of each of said genes an RNA polymerase promoter and a ribosome binding site, and possibly 3' of each of said genes an RNA polymerase terminator.

In the first embodiment (i) above, a preferred embodiment relates to the ribosome binding site of each of the genes, which is its natural ribosome binding site, and it is thus preferred to use at step (b) a translation extract prepared starting from the organism from which the sample of nucleic acids comes or from a phylogenetically close organism.

In the second embodiment (ii) above, the ribosome binding site can be the natural site of each of the genes or another ribosome binding site better adapted to the translation step (b).

A variation of the first (i) and second (ii) embodiments above consists of carrying out, in parallel or simultaneously, the previously described method of the invention when the analyzed function corresponds to a single protein, each step (a) being carried out with each of the genes. An alternative to the carrying out of the methods of the invention simultaneously or in parallel, consists in separately carrying out for each of the genes the steps (a) and (b), then, for the final detection and/or measurement of the function implicating each of the proteins, collecting the products of the steps (b) in order to carry out step (c).

In the same way, when the analyzed function corresponds to proteins whose genes are physically separate on the genome, the method of the invention consists in realizing in parallel or simultaneously, the method described previously when the analyzed function corresponds to only one protein, each stage (a) being realized with each gene. An alternative to the realization in parallel or simultaneous of the methods of the invention, consists in realizing separately for each gene, the stages (a) and (b), then, for the detection and/or the final measurement of the function implying each protein, to gather the products of the stages (b) to carry out stage (c).

The invention also relates to a method of quantifying a known function, to starting from nucleic acids present in said sample, characterized in that it includes:
 a) At (c) the measurement of said function according to steps (a) to (c) above, then
 d) The comparison of the measurement of the function possibly is present in the sample carried out at step (c) with a standard value or a collection of standard values of said function measured on one or several standard samples according to a measuring process identical or equivalent to that of step (c).

A standard sample for the carrying out of step (d) above can be any sample containing:
 A quantity, advantageously known, of the gene or genes coding for the protein or proteins corresponding to the function analyzed by the method of the invention, and that will thus be subjected to a treatment of transcription and translation as in step (b), then the function of the protein or proteins obtained will be measured according to a process of measurement identical or equivalent to that of step (c),
 A quantity, advantageously known, of the protein or proteins corresponding to said function, which will be measured according to a measuring process identical or equivalent to that of step (c),
 A quantity, advantageously known, of one or several organisms or process possessing the gene or genes coding for the protein or proteins corresponding to said function, which will be measured according to a measuring process identical or equivalent to that of step (c).

The standard sample can come from a medium identical or different from that in which the steps (a) to (d) of the method of the invention are carried out. It can relate to the same medium but taken at a different moment.

In a particular form of the method of carrying out the method of the invention, the sample can itself contain the standard.

It can also be evaluated notably as compared to a predetermined threshold or as compared to a standard curve permitting the comparison of measurements of the function of step (c) with those of the standard samples.

In the scope of the different embodiments of the present invention, the preparation of the sample at step (a) of the method of the invention consists of placing one or several nucleic acid sequences coding for the protein or proteins corresponding to the analyzed function that one wishes to detect or quantify under the control of elements necessary to the in vivo transcription and translation.

Thus, at step (a), the control sequences of the gene or genes coding for the protein or proteins corresponding to the detected and/or quantified function according to the process of the invention are for the transcription:
 A 5' RNA promoter of the strand coding for said gene or genes,
 Possibly a 3' RNA polymerase terminator,
and for the translation:
 A ribosome binding site that may or may not be the natural binding site or sites of the gene or genes.

The promoter (5') and the terminator (3') if it is present, of an RNA polymerase, are for example those of the RNA polymerase of the phages T7, SP6, Qβ or λ.

An advantageous embodiment of step (a) of the method of the invention consists of preparing the nucleic acid molecule or molecules by an amplification reaction with the gene or genes coding for the protein or proteins corresponding to the analyzed phenotype, starting from the sample of nucleic acids. It can relate to an amplification by PCR or by techniques derived from PCR of the RT-PCR type, nested PCR, multiplex PCR, or techniques different from PCR such as NASBA, SDA or rolling circle type and others. Advantageously this preparation makes use of a couple of oligonucleotides or a couple of specific primers of the nucleic acid molecule or molecules comprising the gene or genes coding for the protein or proteins corresponding to the analyzed function. This preparation by amplification is carried out with the help of one or several pairs of primers, each one comprised of for the PCR (FIG. 1) and NASBA examples:
 For the sense primer, some of the sequence hybridizing upstream of one or several nucleic acid molecules comprised of the gene or genes coding for the protein or proteins corresponding to the analyzed function, and of an RNA polymerase promoter and optionally a ribosome binding site, and
 For the antisense primer, some of the sequence hybridizing downstream of one or several nucleic acid molecules comprised of the gene or genes coding for the protein or proteins corresponding to the analyzed function, and optionally an RNA polymerase terminator.

Step (a) can be carried out by any other appropriate technique. In effect, the preparation of the nucleic acid molecule of step (a) can be carried out by any other method known to a person skilled in the art as for example a restriction cutting permitting recovery of the gene or genes of interest followed by an ordered ligation with the control elements necessary for the in vitro transcription and the translation previously indicated.

When the invention relates to the detection or the quantification of at to least two functions in the same sample, whatever is the technique of preparation of the nucleic acid molecule or molecules at step (a), they can be implemented with discriminating or non-discriminating primers.

In this way, when at step (a) non-discriminating primers are used, then at step (c) said functions are detected and/or measured by functional tests permitting differentiation of said functions.

Or, when at step (a) discriminating primers are used, then at step (c) said functions are detected and/or measured by functional tests permitting or not permitting differentiation of said functions.

In the case of using couples of primers at step (a) for the preparation of nucleic acid molecules, different forms of implementation of the method of the invention can be carried out. It is possible to combine in a single tube or not two detection reactions and/or quantifying. Step (a) is then carried out with the necessary amplification primers specific for the target genes. In this case, two different functional tests can be used to detect and/or quantify each of the functions. It is still possible to use the same functional test for the functions, and a positive result thus uniquely indicates the presence of one or the other of the target proteins. It is therefore possible to use as many functional tests as target proteins, each different reporter permitting the revealing of each one of the target proteins.

It is possible to use discriminating or non-discriminating primers at step (a) and/or different or non-different functional tests at step (c) in the method of the invention (example I).

Discriminating primers permit specific isolation of a nucleic acid sequence coding for a protein corresponding to a representative function of a process or of an organism, whereas the non-discriminating primers do not necessarily permit specific isolation of a gene coding for such a function.

In the case of using non-discriminating primers at step (a) of the method of the invention, the specificity of the process or of the organism will be determined by a functional test or by a combination of functional tests carried out at step (c) of the method of the invention. The non-discriminating primers can be universal or non-universal, degenerate or non-degenerate. It is understood that by degenerate primers is meant primers that are partially hybridized to the nucleotide target coding for the protein corresponding to the sought-after function. It is equally understood that by non-discriminating primers is meant pools of discriminating primer couples for preparing at step (a) the nucleic acid molecule or molecules comprising the gene or genes coding for the protein or proteins corresponding to the sought-after function present in one or several processes or one or several organisms.

It is possible to carry out the method of the invention by combining discriminating and non-discriminating primers at step (a) with specific or non-specific functional tests at step (c) in order to carry out the detection and the quantifying of a process or of an organism. In effect, it is the interpretation of these different tests that permits determination of the specificity of the detection.

The method of the invention permits analysis of the different functions corresponding to the expression of several mutants of a single gene that can be contained in a single initial nucleic acid sample. By way of example of this application of the method of the invention, there can be cited the different mutants of the gene of the HIV protease contained in a sample of a patient infected by this virus. The implementation of the method of the invention thus consists of the carrying out each step (a) with each of the mutants of said gene in such a way to express each of the latter separately. The separation of the mutants contained in the sample can be carried out by cloning, extreme dilution or by any other method known by a person skilled in the art. This application of the method of the invention therefore consists of analyzing the different forms of a known function contained in a single sample of nucleic acids. By different forms of a known function is understood the demonstration of comparable properties, for all the variants of the HIV protease have a proteasic activity, but distinguishable from each other, since each proteic variant of the HIV protease can have a specific resistance to an antiprotease.

The invention therefore also relates to the application of the method to the detection and/or the quantifying in vitro of the different forms of a known is function in a sample of nucleic acids liable to contain the gene or genes coding for the protein or proteins corresponding to these different functions. In effect, as indicated above for the HIV protease, the sample of a patient infected by this virus can contain several variants of the virus, each one expressing a different protease. It is therefore interesting to carry out not only a diagnosis of the presence of the virus by the intermediate of the search for the function of the viral protease in accordance with the method of the invention, but also to carry out an analysis of the representation of the different variants of this protease.

Based on this example for HIV, the invention permits the analysis in vitro of different forms of a known function corresponding to the expression of several variants of a gene that can be contained in a single initial sample of nucleic acids. This goal is attained according to the invention, by optionally amplifying the different variants, for example by cellular culture or by molecular amplification, then by isolating each gene, for example by cloning or by extreme dilution, and by expressing each of these genes in accordance with the steps (a) and (b) of the method of the invention, and finally by revealing the sought-after function or functions.

The transcription and translation reactions (step b) can be simultaneous, which means that the translation phase is carried out simultaneously with the transcription, or broken up into two distinct steps of transcription and translation.

The decoupling of the transcription and translation steps permits optimization of the yields of each step, and thus production of higher quantities of protein, which finds all its utility in the case of the detection of enzymes with low specific activity.

This decoupling also permits the standardization of the formation of the products at step (b) and enables later comparison of the different expressed functions.

The decoupling between transcription and translation equally permits avoiding the problems of degradation of the DNA matrix by nucleases if it was prepared by PCR. In effect, the components of the transcription reaction are less contaminated by nucleases, contrary to the translation extracts.

The decoupling also permits the use of different translation extracts according to the origin of the targeted DNA. In effect, translation of the transcript is advantageously carried out with a translation extract of the same origin or of an origin close to that of the biological sample on which the process of the invention is practiced. Thus, the adequacy between the origin of the signals of translation of the transcripts and the cellular extract are optimized for optimal translation efficiency. There can be cited by way of example the use of a translation extract prepared starting from eukaryote cells for the translation of a eukaryotic target sequence or of a translation extract prepared starting from non pathogenic mycobacteria for the translation of *Mycobacterium* pathogen genes such as the RecA intein of *Mycobacterium tuberculosis*. In another case of figure, the translation extract is prepared starting from extremophile organisms for the translation of a gene of same organism or of another extremophile organism of the same type (thermophiles, halophiles, acidophiles, etc.). These respective extracts are able to improve the efficiency of the process. These extracts are chosen for their capacity to translate the transcripts.

The process of the invention is notable in that it implements appropriateness between the expression punctuation of the transcripts and the translation extracts used. These extracts are also characterized in that they either do not contain the sought-after property, or they contain it but that it is not detectable in the test conditions carried out for detecting the sought-after function. It relates for example to the use of a translation extract containing a mesophilic beta-galactosidase activity permitting translation of beta-galactosidase thermopile mRNA and the detection of the activity of this latter at high temperature, which eliminates the mesophilic beta-galactosidase activity.

According to the genetic origin of the nucleic acid molecules prepared at step (a), for example DNA of Gram positive or negative microorganisms, of eucaryotes, of viruses etc, and of the tested function, different translation extracts can therefore be used.

A particular embodiment of the process of the invention consists of using at step (b) a translation extract that is in fact a mixture of several translation extracts. It can relate, for example, to an *E. coli* translation extract overexpressing a chaperon protein A mixed with an *E coli* translation extract overexpressing a chaperon protein B. Any type of mixture is conceivable from the moment it corresponds to the characteristics described above. In the same way, it is possible to use a translation extract in which one or several specific tRNAs of one or several codons is added. The translation extracts obtained in this way thus permit translation of the mRNA containing these specific codons, such as for example the translation of an mRNA containing an amber codon by adding in the translation extract one or several suppressor tRNAs.

The treatment of step (b) with a translation extract can also be carried out with a standard translation extract whatever be the origin of the sample such as for example an *E. coli* extract and/or any other cellular extract or extracts which are supplemented or not by molecules of interest such as those, for example, indicated previously (tRNA, chaperon . . . ).

It is equally possible to add to the translation extract of step (b) one or several substances favoring refolding or a more effective maturation of the expressed proteins, such as for example chaperons, detergents, sulfobetaines, membrane extracts, etc.

In the case where the target sequence is of the eucaryote type, the transcription reaction of step (b) can be completed by an in vitro mRNA splicing and maturation reaction by adding a nuclear extract to the reaction mixture.

In the particular case where the reporter gene is co-expressed with the protein or proteins coding for the function or functions, the transcription and translation reaction of step (b) is standardized in such a way so as to avoid results corresponding to false positives or to false negatives:

On the one hand, in order for the target protein coding for the function to have the time to act at the level of the measurement of the function at step (c) such as for example to act on the reporter in order to inhibit it, or to avoid being placed under conditions where the reporter would be in a larger quantity than the target protein.

On the other hand, in order to be placed under conditions of activity for both the target protein and the reporter if it is necessary to the measurement test of step (c).

The method of detection and/or of quantification of a known function which is the object of the invention is notable in that it permits avoiding of false positives due to interference of the components present in the sample starting at the time of the detection and/or the measurement of the analyzed function at step (c). In effect, on account of the principle of the method of the invention, the potential interactions of the compounds of the initial medium on the detection and/or the quantification of the function to detect and/or quantify are reduced (for example by dilution of said initial medium as one goes along the different steps of the process of the invention, but especially by the specificity of the functional test used at step (c) of the process of the invention). Moreover, the method of the invention endeavors to detect and/or quantify a function, all nucleic acid molecules coding for non-functional proteins or all nucleic acid molecules having sequence homology with the sought-after sequence but coding for a different function will not be detected, which is one of the major advantages of the method of the invention as compared to the techniques of the prior art.

The method of the invention offers the advantage of being able to specifically detect one or several target sequences in a sample to be analyzed and to later work directly on this/these target sequence or sequences. The sensitivity of this method can be explained by the multiplier coefficient of the steps (b) and (c) corresponding respectively to the transcription, to the translation of the gene or genes prepared at step (a) then to the detection and/or the measurement of the function corresponding to the protein or proteins produced at step (b). In addition, in order to increase the sensitivity, the method of the invention can go through an amplification step of the transcripts after the transcription step by any technique known to a person skilled in the art such as NASBA (nucleic acid sequence-based amplification) or TMA (Transcription Mediated Amplification) before the translation step. The method of the invention is moreover rapid and reproducible, for all the reactions are carried out in vitro, which permits standardization of the detection and becoming free of all of the problems tied to in vivo diagnostic tests, such as membrane diffusion, cellular toxicity or physiological state of the cells.

It is useful to point out that in this application of the method of the invention, the sought-after function is highlighted thanks to the activity of the target protein that is expressed in vitro. In this case, the method of the invention not only permits the highlighting of one or several functions of a process or of an organism, but also the characterization of the activity of the corresponding protein or proteins. This characterization, can also be designated phenotyping of the expressed protein or proteins according to the process of the invention, as opposed to genomics which is the characterization of the nucleic acid composition of the target sequence. The identification of the target sequences thus equally corresponds to the identification of the function and to its characterization. By characterization is understood for example the definition of the inhibition spectrum of a target protein by specific inhibitors or the definition of a pH range in which the target protein is active. If the function is an enzymatic activity, it also relates to the analysis of the optimal conditions of functioning (pH, temperature, salts concentration), of kinetic parameters (Vm, Km), of inhibition parameters (Ki). If the function is affinity, it can also relate to the determination of the Kd, or of the molecule having the most affinity for this protein. It can also relate to the determination of the size of the translated protein or of the transcribed mRNA, and optionally of the sequencing of the corresponding gene.

By way of example, this method is of particular interest in the diagnosis of the target protein corresponding to aspartic acid proteinase of the HIV virus in order to consecutively study its sensitivity to different specific proteinase or antiviral inhibitors, when the corresponding target sequence is present in a nucleic acid sample.

The characterization of a function represents the determination of the characteristics of said function and in particular the identification of a substance or substances capable of modifying said function or functions. By substance is understood polynucleotides, peptides, proteins, ions, molecules or natural or synthetic chemical compositions, hormones, aromatic compounds, antibodies, antibody fragments, genes, cellular receptors, amino acids, glycopeptides, lipids, glycolipids, sugars, polysaccharides, etc. . . . , capable of modifying the activity of one or several functions of an organism or of a process. These said substances will be able to correspond to one or several leads. It can relate to any agent capable of modifying the function or functions such as anti-viruses, inhibitors, stimulants, physico-chemical conditions, radiation or thermal treatments. This characterization can be carried out on line with detection and/or quantification or in a sequential-manner. This characterization of function permits the carrying out of statistical analyses. In fact, after having identified different functions or different functional variants, it is possible to individually study for example their resistance to one or several substances. This form of embodiment of the method of the invention is advantageously carried out on a microtitration plate or on a chip in order to study for example the behavior of different genetic variants of the aspartic acid proteinase function of HIV1 vis-á-vis several anti-viruses.

Consequently, the method of the invention can comprise after step (c), a test of said function with a substance.

The detection and/or quantifying of different functions present in a sample according to the method of the invention presents a certain advantage in the follow-up of an organism or of a process. In effect, the method of the invention permits detection and/or quantification for example of the functions of a virus and of a cellular constituent. This embodiment of the invention is, for example, of particular interest in the detection and/or quantification of the presence of a pathogen in an organism (virus or bacteria), which can be correlated to the detection and/or quantification of a specific function of said infected organism or of the response to infection of the infected organism (for example production of alpha-1 acid glycoprotein (AAG) in the case of infection by the HIV virus).

The method of the invention moreover permits carrying out of follow-ups of one or several functions in different samples. By way of example, there can be cited the follow-up of different functional variants of different functions characteristic of an infection by the HIV virus. The appearance of different functional variants is characteristic of resistance phenomena to one or several antiviruses. According to the development of this resistance, different tissues will carry different genetic variants of the virus. The follow-up of the different genetic variants in different tissues thus gives an indication of the propagation of the infection. According to the detection results of the different genetic variants in different tissues, the doctor will be able to judge the immune state of a patient and its capacity to fight against opportunistic diseases and moreover to contemplate for the ill person in addition of a treatment by antiviruses, a treatment by antibiotics and or antifungals.

Taking into account the ease, the low cost and the speed of the method of the invention, a follow-up of the function or functions can be implemented in a manner to periodically carry out the detection and the quantification of the function or functions. The comparison of the results obtained at different times and their interpretation permits a follow-up in the time of the evolution of a process.

These different follow-ups permit a practitioner to understand the development of a process or of an organism. The interpretation of the results will permit the practitioner who makes use of the process of the invention to make a decision.

The steps of the process of the invention can be carried out successively or not without interruption or not by the same operator. It can be carried out in an automatic device integrating each of the steps, or different operators can carry it out in a discontinuous fashion, optionally. The samples of nucleic acids can thus be placed on a support that can correspond for example to a biochip or a microtitration plate containing several dozen to several thousands of sites. These supports are designed to permit:

- the preparation of target sequences (step a),
- the initiation of the transcription and translation reactions (step b) and the revelation of the reporter molecule (step c).

Consequently, the invention relates to a device including an arrangement of one or several supports, of robots and of a reader of said supports for the carrying out of the steps of the previously described method.

The invention also relates to a kit for the implementation of the methods previously described.

In a first embodiment a kit according to the invention includes: the means of revealing the function, an RNA polymerase, nucleotide sequences for the preparation of the nucleic acid molecules including the gene or genes permitting the expression of the protein or proteins corresponding to the detected and/or quantified function, the four triphosphate nucleotides, the mixtures necessary for said preparation, for the transcription and the translation, and optionally some controls.

In a second embodiment a kit according to the invention includes:

- Optionally the products necessary for the preparation of the nucleic acid molecules including the gene or genes permitting the expression of the protein or proteins corresponding to the detected and/or quantified function,
- Any support such as microtitration plate or chip containing: the means for revealing the function, an RNA polymerase, the four nucleotide triphosphates, the transcription and translation mixtures, possibly some standards.

The kits and the supports can be contemplated for the detection and/or the simultaneous or non-simultaneous quantifying of one or several function corresponding to one or several processes or one or several organisms.

The invention therefore also has as an object a support having a series of sites for the implementation of a method of the invention, characterized in that each of said sites permits the detection and/or the measurement of a different function.

Other advantages and characteristics of the invention will become apparent in the examples of carrying out the invention, which follow and which make reference to the attached drawings in which:

FIG. 1 is a schematic representation of the method of the invention.

FIG. 2 is a schematic representation of the application of the method of the invention to the diagnosis of the HIV virus.

FIG. 3 is a schematic representation of the application of the invention to the diagnosis of *Mycobacterium tuberculosis*.

FIG. 4 depicts the detection of the total activity or of the activity of polyresistant germs by the method of the invention.

FIG. 5 depicts the detection of the viral load by the method of the invention.

FIG. 6 depicts the characterization of the effect of an inhibitor on a positive sample as compared to a negative standard by the method of the invention.

EXAMPLE I

Examples of Implementing the Method of the Invention with Different Primer Sets at Step (a) of Preparation and/or Different Functional Tests at Step (c) of Detection and of Quantification One or Several Functions The cases hereinafter permit the illustration of different possibilities of the method of the invention.

1) Case No. 1: The primers used at step (a) of the process of the invention permit detection and quantification of the reverse transcriptase activity of the HIV virus.

Table 1 hereinbelow shows that the use of discriminating primers at step (a) of the method of the invention permits detection by a functional test at step (c) of;

- The absence of the reverse transcriptase function in sample 3, therefore the absence of the HIV virus.
- The presence of the reverse transcriptase function in samples 1 and 2, therefore the presence of the HIV virus in samples 1 and 2. The HIV virus is present in larger quantity in sample 2 than in sample 1.

TABLE 1

|  | Sample 1 | Sample 2 | Sample 3 |
|---|---|---|---|
| Discriminating primers are used at step (a) | + | +++ | − |

2) Case No. 2: Non-discriminating primers are used at step (a) of the method of the invention in order to detect in each sample the potential presence of reverse transcriptase activity.

Table 2 hereinbelow shows that the use of non-discriminating primers at step (a) of the method of the invention permits detection by a functional test at step (c):

The absence of reverse transcriptase function in sample 3, therefore the absence of virus.

The presence of reverse transcriptase function in samples 1 and 2, therefore the presence of virus possessing a reverse transcriptase function in samples 1 and 2. The reverse transcriptase function is present in larger quantity in sample 2 than in sample 1.

Table 2 hereinbelow also shows that the use of discriminating primers at step (a) of the method of the invention permits detection by a functional test at step (c):

The presence of HIV in sample 1.
The presence of HBV in sample 2.

TABLE 2

|  | Sample 1 | Sample 2 | Sample 3 |
|---|---|---|---|
| Non-discriminating primers | + | +++ | − |
| Specific primers of HIV RT | + | − | − |
| Specific Primers of HBV RT | − | +++ | − |

3) Case No. 3: Different functional tests are implemented at step c of the process of the invention for detecting a polymerase according to its thermoresistance.

Table 3 hereinbelow shows that the method of the invention permits detection by different functional tests at step (c):

The presence of a polymerase preferentially active at 100° C. in sample 1.
The presence of a polymerase active at 60° C. in sample 2.
The presence of a polymerase active only at 100° C. in sample 3.

TABLE 3

|  | Sample 1 | Sample 2 | Sample 3 |
|---|---|---|---|
| Functional Test at 60° | + | +++ | − |
| Functional test at 100° | ++++ | + | +++ |

4) Case No. 4: A functional test can be carried out in the presence of different substrates in order to detect and quantify the different functions present in a sample. This functional test can permit, for example, the detection of a polymerase activity.

Table 4 hereinbelow shows that the method of the invention permits detection by a functional test carried out at step (c):

The presence of DNA dependent and RNA dependent DNA polymerase activity in sample 1.
The presence of DNA dependent DNA polymerase activity in sample 2.
The presence of RNA dependent DNA polymerase activity in sample 3.
The functional test in the absence of substrate is a negative control permitting validation of the detection.

TABLE 4

|  | Sample 1 | Sample 2 | Sample 2 |
|---|---|---|---|
| Functional Test +DNA | + | + | − |
| Functional Test +RNA | + | − | + |
| Functional Test without substrate | − | − | − |

5) Case No. 5: This case represents for example the detection of the HIV virus in blood samples 1, 2 and 3. Two functional tests are carried out to control the specificity of our detection.

Table 5 hereinbelow shows that the use of a pool of discriminating primers at step a) of the method of the invention on different blood samples permits detection by different functional tests carried out at step (c):

The presence of HIV in sample 1
The absence of HIV in sample 3
An error in sample 2

TABLE 5

|  | Functional test permitting revelation of reverse transcriptase activity | Functional test permitting revelation of aspartic acid proteinase activity |
|---|---|---|
| Test 1 | + | + |
| Test 2 | + | − |
| Test 3 | − | − |

6) Case No. 6: This case relates to the detection and quantifying of the following microorganisms

*Aeromonas hydrophila* is characterized by ONPG, LDC, ESC, OX activities.

*Escherichia coli* 1 is characterized by ONPG, LDC, ODC, UE.

*Salmonella arizonae* is characterized by ONPG, LDC, ODC.

*Vibrio alginolyticus* is characterized by LDC, ESC, OX.

Table 6 hereinbelow shows that the use of a discriminating primer pool at step (a) of the method of the invention on different samples permits detection by different functional tests at step (c) and according to different functional identity cards of the microorganism of:

The presence of *Aeromonas hydrophila* in sample a.
The presence of *E. coli* 1 in sample b.
The absence of microorganisms in sample c.
The presence of *Vibrio alginolyticus* in sample d
The presence of *Salmonella arizonae* in sample e.

TABLE 6

|  | ONPG | LDC | ODC | UE | ESC | OX |
|---|---|---|---|---|---|---|
| Sample a | +++ | + | − | − | + | +++ |
| Sample b | +++ | +++ | ++ | + | − | − |
| Sample c | − | − | − | − | − | − |
| Sample d | − | + | − | − | ++ | +++ |
| Sample e | +++ | +++ | +++ | − | − | − |

It is understood in Table 6 by:
ONPG: beta D-galactosidase
LDC: Lysine decarboxylase
ODC: Ornithine decarboxylase URE: Urease
ESC: beta-galactosidase
OX: Cytochrome oxidase

EXAMPLE II

Diagnosis of HIV Virus

Among the viral proteins necessary to the multiplication cycle of the HIV virus, aspartic acid proteinase can be noted. The presence of this protein can serve to diagnose the infection of a patient by the retrovirus.

Figure 2:
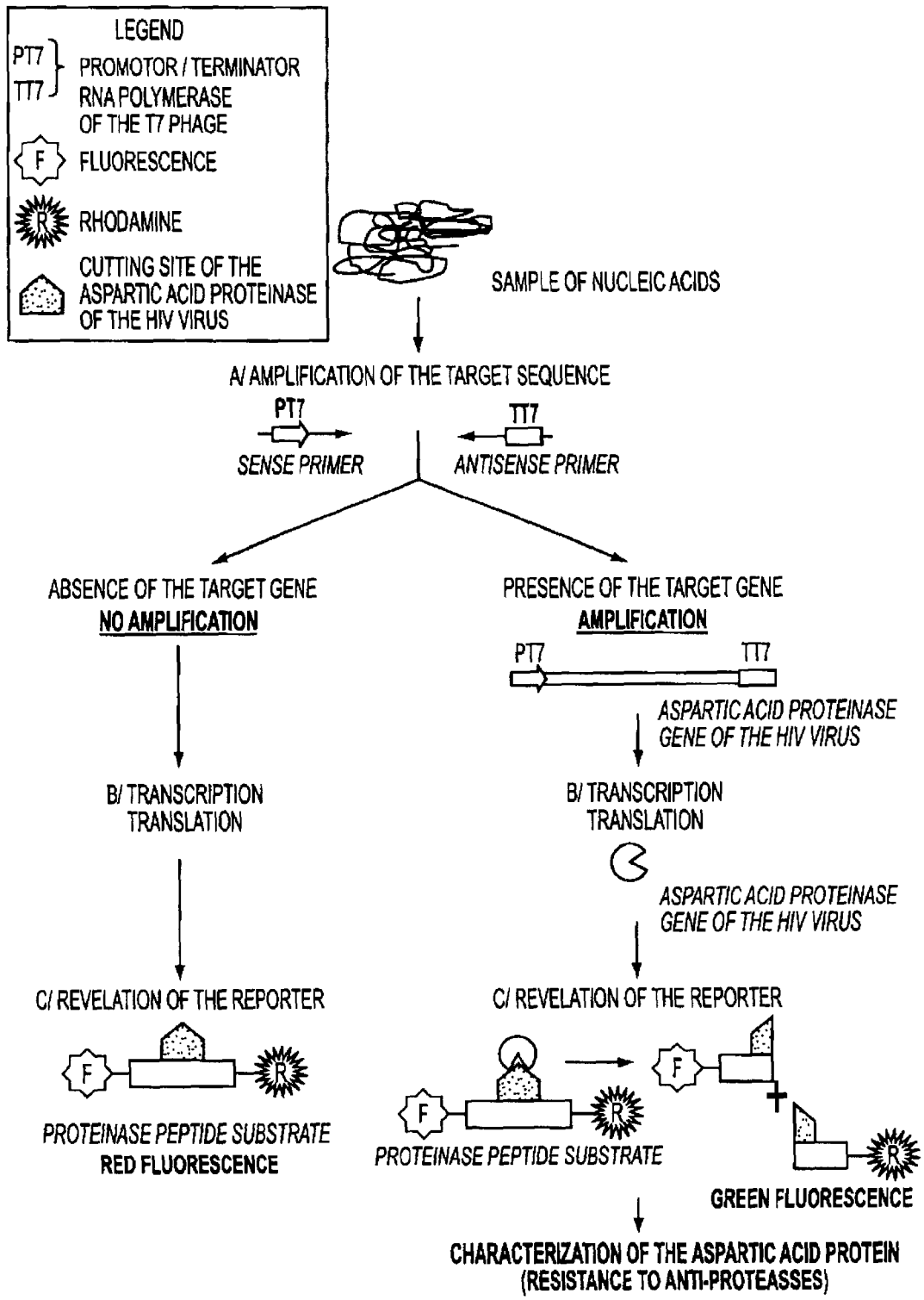
Figure 3:
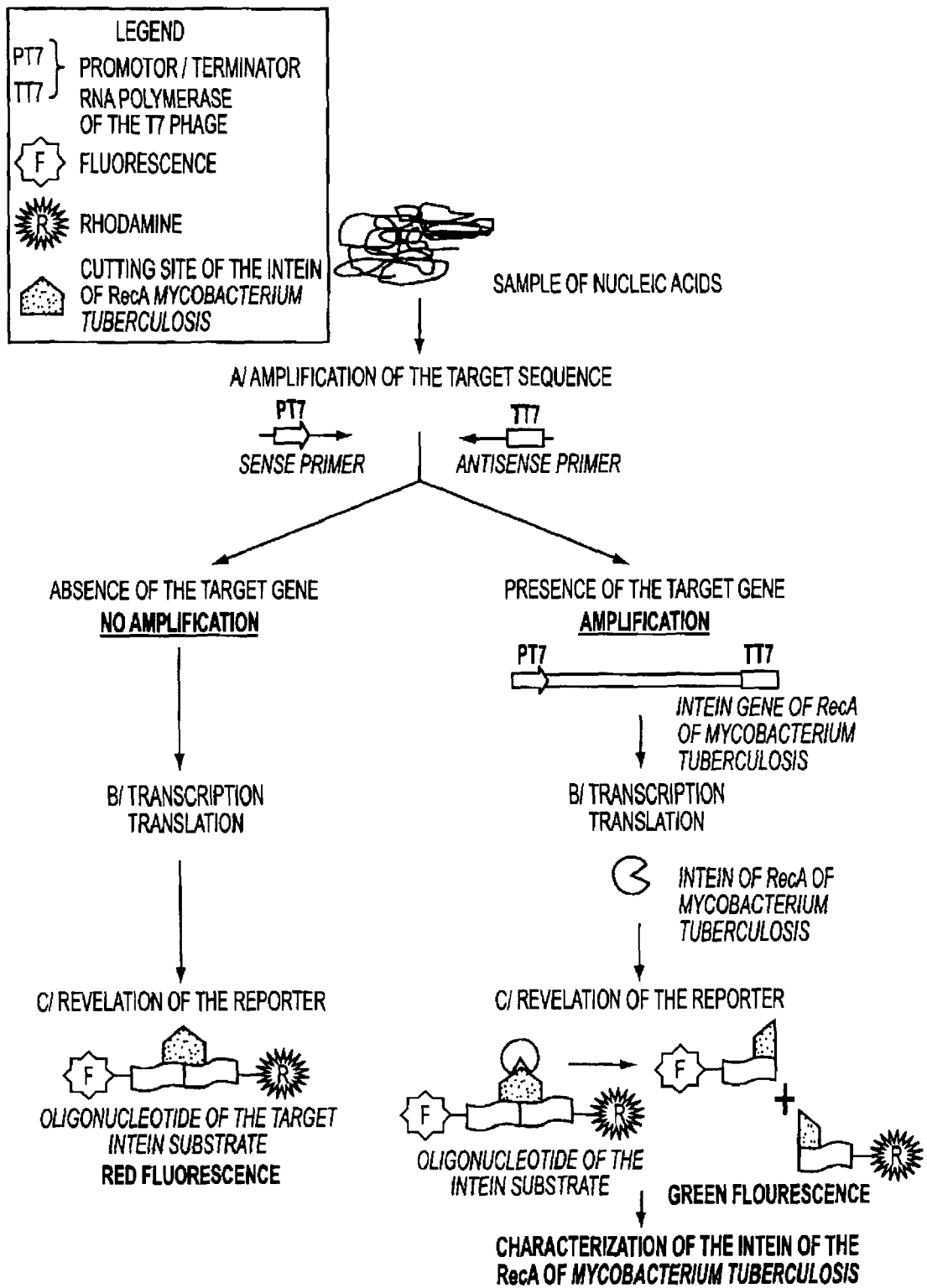

As shown in FIG. 2, after an extraction of the nucleic acids from a blood sample, an amplification step permits amplifying the gene of the HIV aspartic acid proteinase if the patient is infected by the virus and integrating the promoter, the terminator of the RNA polymerase T7 and an RBS site at the target sequence.

The reporter molecule prepared at step (a) is a peptide containing specific cutting sites of HIV proteinase. This peptide is covalently bonded respectively at its N and C terminus to a fluorescent molecule (as for example fluorescein) and to a quencher of this latter (as for example rhodamine).

The amplified target gene is placed in a tube (charged with) containing (loaded with) a mixture for coupled transcription/translation (constituents necessary for transcription and translation). Then the reporter molecule is added. Advantageously, the transcription and translation reaction medium is composed either of an E. coli translation cellular extract or a translation cellular extract of eucaryotic cells.

If the aspartic acid proteinase is absent from the tested sample, the reporter is not cleaved. The fluoresceine and the rhodamine are thus found in a sufficiently close environment to assure an energy transfer of the FRET type (fluorescence resonance energy of transfer). After exposure of the reporter peptide to a given wavelength (about 490 nm), only the fluorescent red of the quencher will be detectable.

If the aspartic acid proteinase is present in the tested sample, the reporter is cleaved. The fluoresceine and rhodamine are thus too far apart to assure an energy transfer. After exposure of the cleavage products to a given wavelength (about 490 nm), only the green fluorescence of the fluoresceine is detectable.

Negative and positive controls are carried out in parallel. They correspond respectively to a PCR reaction fraction carried out on the DNA of a healthy patient and of an infected patient.

After having diagnosed the presence of the virus of a patient, this method permits a consecutive test for characterization of the aspartic acid proteinase: according to the strain responsible for the viral infection, the aspartic acid proteinase has a variable sensitivity to different specific inhibitors. Such a phenotyping of the aspartic acid proteinase will permit adaptation of the therapy of the patient directly after the diagnosis of the viral infection. For this, it is sufficient to incubate a fraction of the amplification reaction in different transcription/translation reactions, each one containing a specific aspartic acid proteinase inhibitor currently used in antiviral therapies and to then carry out the aspartic acid proteinase activity test with the FRET peptide.

EXAMPLE III

Specific Detection of an Element within a Sample Containing Similar Elements

1) Specific Detection of an Element within a Sample Containing Similar to Elements.

The β-lactamines (penicillins and cephalosporins) represent the class of antibiotics that are the most used in anti-infection therapy. Since the introduction of these molecules in therapy, new resistances to these compounds is developing, favoring the expansion of nosocomial infections. Among the different resistance mechanisms acquired by the germs, one of the most important consists in the production of an enzyme (β-lactamase TEM-1 (Sutcliffe J. G., 1978, Nucleotide sequence of the ampicillin resistance gene of Escherichia coli plasmid pBR322, Proc. Natl. Acad. Sci. USA, 75, 3737-3741) for certain enterobacteria for example, or beta-lactamase PSE for Pseudomonas aeruginoas) capable of hydrolyzing the antibiotic before it was able to act. There exist some β-lactamase inhibitors used synergistically with an antibiotic, but as one goes along with their use, new forms of β-lactamases resistant to these inhibitors appear.

The detection of the function of these enzymes therefore represents an excellent test for the diagnosis of the presence of germs resistant to antibiotics. On the other hand, the specific detection of beta-lactamases resistant to inhibitors is particularly advantageous, because it permits directly knowing if polyresistant (antibiotics and inhibitors) organisms are contaminating a sample, which permits rapid adaptation of therapy.

This experiment permits the specific detection of polyresistant (resistance to antibiotics and resistance to a beta-lactamase inhibitor: clavulanic acid) germs expressing a TEM-1 resistant variant, in a sample contaminated by monoresistant germs (resistant only to antibiotics).

10 μl of culture at DO600.2.3 were centrifuged and each pellet was resuspended into 12 μl of cellular lysis buffer (10 mM Tris HCl pH 7.5, 1 mM EDTA, 50 μg/ml proteinase K) and incubated 15 minutes at 55° C. then 15 minutes at 80° C. 9 μl of each of these lysates was added to a PCR amplification mixture that permitted amplification of the gene conferring monoresistance and of the gene conferring polyresistance, as well as of the sequences permitting their in vitro expression. 5 μl of each PCR amplification were used to carry out an in vitro transcription as described by Gurevich et al. (Gurevich V. A., Pokrovskaya I. D., Obukhova T. A. and Zozulya S., 1991, Preparative in vitro mRNA synthesis using SP6 and T7 polymerases, Anal. Biochem., 195, 207-213) 10 μl of each transcription was used to translate in vitro the proteins as described by Zubay (Zubay G., 1973, In vitro synthesis of protein in microbial systems, Ann. Rev. Genet., 7, 267-287) to a final volume of 100 μl

TABLE 8

| Sample | 1 | 2 | 3 | 4 | 5 | 6 | 7 |
|---|---|---|---|---|---|---|---|
| % of germs resistant to antibiotics | 100 | 90 | 70 | 50 | 30 | 10 | 0 |
| % of germs resistant to antibiotics and to clavulanic acid | 0 | 10 | 30 | 50 | 70 | 90 | 100 |

Two types of activity tests were carried out:
A measurement of the "total" beta-lactamase activity by using as substrate a chromogenic antibiotic: nitrocephine. 10 μl of the translation mixture were incubated at 37° C. in a final volume of 1 ml of activity revelation buffer (final concentration: NaP 50 mM pH 7.0, 100 μl/ml of nitrocephine and 0.25 mM DMSO). The reaction was followed by monitoring absorbance changes at 486 nm.
A measurement of the "resistance to clavulanic acid" activity by using as substrate a chromogenic antibiotic: nitrocephine and a given concentration of clavulanic acid. 10 μl of the translation mixture were incubated at 25° C. for 3 minutes in a final volume of 1 ml of buffer I (final concentration: 50 mM NaP pH 7.0, 1 μl clavulanic acid). Then 100 μg/ml of nitrocephine and 0.25 mM final of DMSO were added, and the reaction was followed by spectrophotometry at 486 nm.

The results are displayed in Table 8, which indicates the composition of the samples.

Figure 4:
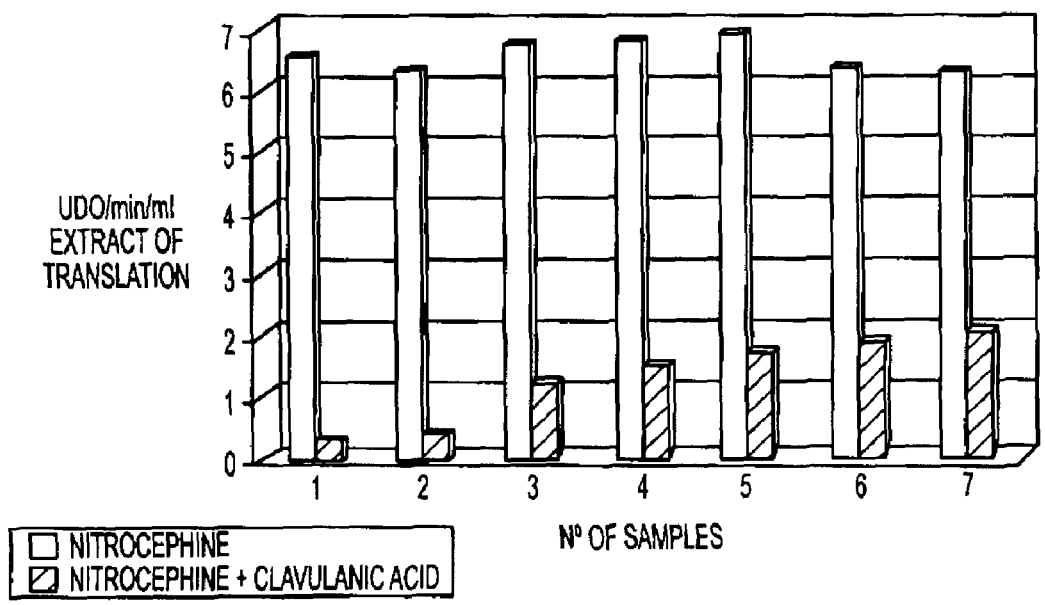

FIG. 4 indicates that the total beta-lactamase activity is detected in all the samples with a comparable level of activity: the test therefore permits simultaneous detection of two functions (antibiotic resistance and antibiotic/clavulanic acid resistance).

When the detection test is carried out in the presence of clavulanic acid, no activity is detected in sample 1 (0% of germs having the double resistance), and an increasing activity is detected for samples 2 to 7 containing from 10 to 100% of germs having double resistance. This functional detection test is therefore highly discriminating since it permits detection of the activity of polyresistant germs within a population of monoresistant germs.

It should be noted that the difference between the total activity detected in a sample and that detected solely for the polyresistant germs is not equal to the activity of the monoresistant germs, because the enzymes of these two types of germs do not have the same specific activity. By knowing these specific activities, it would be possible to make this correlation and to deduce the activity of the monoresistant germs by just knowing the total activity and that of the polyresistant germs.

The method of the invention therefore permits:

To carry out a discrimination by function (revelation of the clavulanic acid resistance function)

To get rid of background noise (specific detection of a population of germs within a population of similar germs)

To characterize a sample: the first functional test reveals that samples 2 to 7 for example are positive, and the second functional test permits revelation that they contain polyresistant germs.

In a much more traditional manner it is contemplated to discriminate between two identical functions (HBV protease function and HIV protease function) by a specific amplification of the gene or genes of one of these (using for example specific PCR primers of the HIV protease gene to detect it within a sample that can also contain the HBV protease gene). In this case the functional test is not necessarily discriminating.

2) Detection of HIV-1 Virus by the Intermediate of its Protease Function

The viral charge of HIV-1 is measured in different samples.

The steps (a) and (b) of the process of the invention were carried out. The detection of the protease activity (step c) was carried out by incubating at 37° C. 10 μl of each one of these translations (step b) with 60 μl of buffer (2 M NaCl, 12 mM EDTA, 200 mM sodium acetate, 2 (MM) mM DTT and 20% DMSO) and 10 μM final of the peptide substrate BACHEM M1865 SEQ ID NO: 1 peptide) on a final volume of 120 μl. This peptide FRET has as a property to release from fluorescence while it is cleaved by the protease of virus HIV. A positive diagnosis is thus characterized by the appearance of the fluorescent signal while it is exposed to UV.

Figure 5:
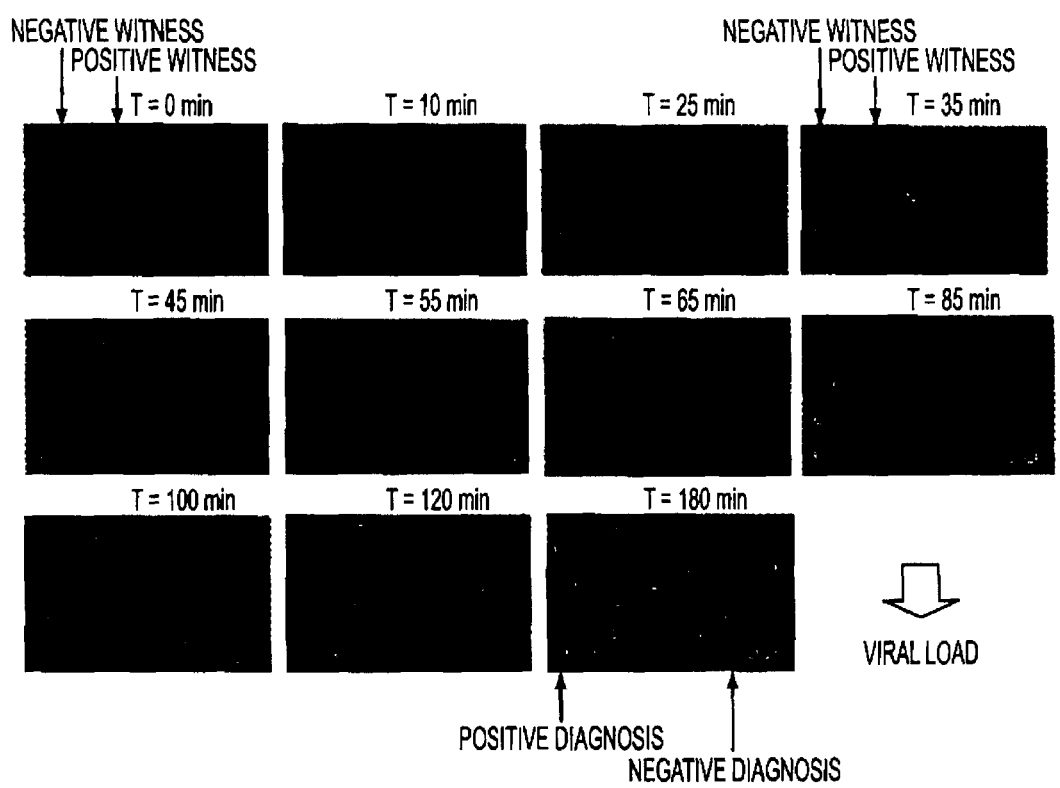
Figure 6:
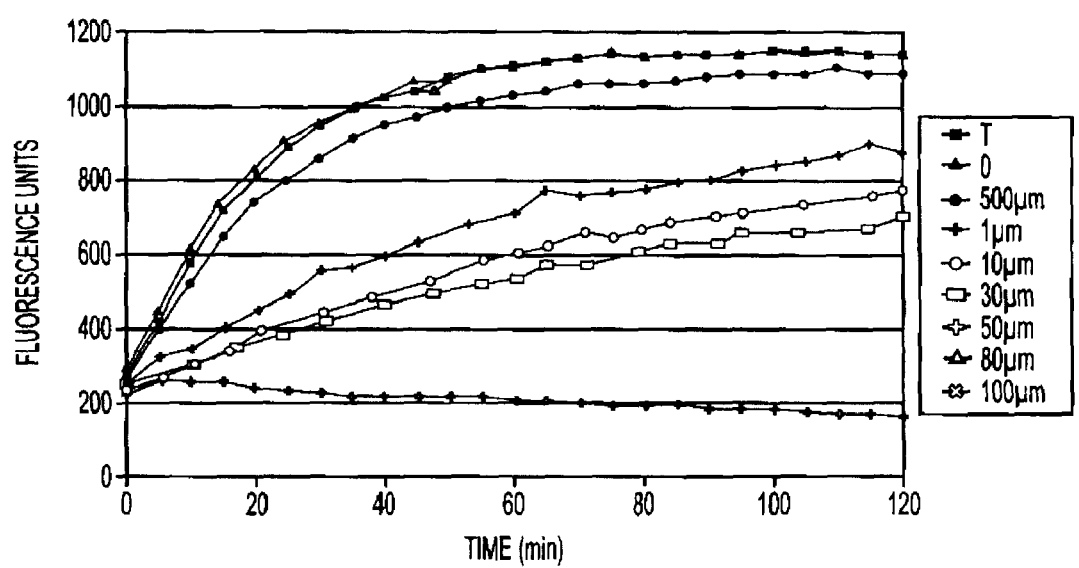

FIG. 5 illustrates the signals obtained for the various samples taken in the course of time. The intensities of fluorescence obtained for the various positive signals correspond to the various viral loads. While referring to a range standard, it is thus possible to quantify the measured signal and to deduct the quantity from virus in each sample.

Once this sample is detected as being positive, the diagnosis by the process of the invention makes it possible to characterize the detected function. FIG. 5 illustrates the effect increasing concentrations of an inhibiting of protease HIV (inhibiting nontherapeutic: the pepstatine A) on the activity of the protease of the sample.

For that, 10 μl of a translation corresponding to a sample were incubated with 37° C. with 60 μl of buffer (2 M NaCl, 12 mM EDTA, 200 mM acetate of sodium, 2 mM DTT and 20% DMSO), 10 μM of peptide substrate BACHEM M1865 SEQ ID NO: 1 peptide) and 0 or 500 nM or 1 μM or 10 μM or 30 or 60 μM or 80 μM or 100 μM final of pepstatin A for a final volume of 120 μl. The reading was carried out by fluorimetry at an excitation wavelength of 340 nm and an emission wavelength of 490 nm.

A correlation between the decrease of the activity and the increase of the rising inhibitor concentrations can be observed.

By fixing a sensitivity (or resistance) threshold (for example 50% of the activity lost for an incubation of 30 minutes with 50 mM of inhibitor), it is possible to determine if this protease is or is not sensitive to the existing protease inhibitors and to directly adapt a therapy relative to the withdrawn sample.

This demonstrates that the method of the invention permits detection, quantifyication and characterization of a function of an organism or of a process starting from a single sample.

These experiments can be carried out with any type of specific to functions of different organisms, or of the same organism, which thus permits characterization of different therapeutic targets (simultaneous detection and characterization of the protease and of the reverse transcriptase of the HIV virus for example).

The invention claimed is:

1. A method for diagnosing the presence of an organism or an infection, or presence of cells or contaminants in a crude biological sample wherein the presence of said organisms, infection, cells or contaminants is unknown by detecting and/or measuring an enzymatic function of one or more proteins comprising the following steps:
- a) preparing nucleic acid molecules from the crude biological sample comprising one or more genes coding for said one or more proteins corresponding to said enzymatic function and control sequences necessary for transcription and translation of said one or more genes;
- b) transcribing and translating in vitro the nucleic acid molecules prepared at step (a) to produce said one or more proteins if present;
- c) detecting and/or measuring the enzymatic function corresponding to said one or more proteins produced at step (b) wherein said detection and/or measuring is carried out with the aid of one or more reporter molecule(s), wherein said one or more reporter molecule(s) is present at one or more of steps (b) or (c), and optionally present at step (a), and wherein said one or more reporter molecule(s) detects the presence of said function; and
- d) diagnosing said presence of said organism or infection, or said presence of said cells or contaminants,
  wherein the presence of said organism or infection, or said presence of said cells or contaminants is unknown prior to performing steps a) through d),
  wherein the biological sample is taken from blood, tissues, urine, or any other bodily fluid, and
  wherein said method is performed without molecular cloning.

2. The diagnosis method according to claim 1, wherein the one or more reporter molecules are produced during step (b) conjointly with the one or more proteins, wherein a reporter gene is placed under the same transcription and translation regulation control sequences as the one or more genes.

3. The diagnosis method according to claim 1, wherein said function corresponds to one protein, and wherein step (a) further comprises adding an RNA polymerase promoter, a ribosome binding site 5' of said gene, and optionally an RNA polymerase terminator 3' of said gene to said nucleic acid molecules, wherein step (b) optionally occurs in the presence of one or more reporter molecules, and wherein the one or more reporter molecules detects and/or measures said function in step (c).

4. The diagnosis method according to claim 1, wherein said function corresponds to several proteins whose genes are located on the same DNA fragment or at different places of the genomic DNA.

5. The diagnosis method according to claim 4, wherein said genes form an operon.

6. The diagnosis method according to claim 5, wherein step (a) further comprises adding an RNA polymerase promoter 5' of the genes of the operon, optionally an RNA polymerase terminator 3' of the genes of the operon, and natural ribosome binding sites for the genes to said nucleic acid molecules.

7. The diagnosis method according to claim 6, wherein ribosome binding sites of each of the genes are natural ribosome binding sites, wherein a translation extract is used in step (b), and wherein the translation extract is prepared from an organism.

8. The diagnosis method according to claim 4, wherein the function corresponds to several proteins whose genes are separated in the genome, and wherein step (a) further comprises adding an RNA polymerase promoter, a ribosome binding site 5' of each of said genes, and optionally an RNA polymerase terminator 3' of each of said genes to said nucleic acid molecules.

9. The diagnosis method according to claim 8, wherein ribosome binding sites are natural ribosome binding sites of each of the genes or non-natural ribosome binding sites.

10. The diagnosis method according to claim 1, wherein after said function is detected and/or measured in step (c), said method further comprises before step (d), the step of quantifying said function comprising comparing the detection and/or measurement of the function with a standard value or several standard values of said function detected and/or measured on one or more standard samples according to a detecting and/or measuring process identical to or substantially similar to a detecting and/or measuring process used in step (c).

11. The diagnosis method according to claim 1, wherein the nucleic acid molecules are prepared by an amplification reaction of the one or more genes.

12. The diagnosis method according to claim 11, wherein the amplification reaction is PCR or NASBA and is carried out with the aid of one or more pairs of primers,
  wherein a sense primer comprises a sequence hybridizing upstream of one or more nucleic acid molecules comprising the one or more genes, an RNA polymerase promoter, and optionally a ribosome binding site, and
  wherein an antisense primer comprises a sequence hybridizing downstream of one or more nucleic acid molecules comprising the one or more genes, and optionally an RNA polymerase terminator.

13. The diagnosis method according to claim 1, wherein after step (b), said method further comprises a step of amplifying a transcript.

14. The diagnosis method according to claim 1, wherein after step (c), said function is tested with a substance that modifies the activity of said function.

15. The diagnosis method according to claim 1, wherein the biological sample is a raw biological sample.

16. The diagnosis method according to claim 1, wherein the function corresponds to an enzymatic activity.

17. The diagnosis method according to claim 1, wherein the organism is a virus, bacteria, algae, fungi, or any product comprising synthetic or natural nucleic acids that express the function.

18. The diagnosis method according to claim 1, wherein said method is a method of diagnosing the presence of virus or bacteria.

19. The diagnosis method of claim 18, wherein said method is a method of diagnosing the presence of an antibiotic-resistant bacterium.

* * * * *